United States Patent [19]

Wong et al.

[11] Patent Number: 4,627,851
[45] Date of Patent: Dec. 9, 1986

[54] COLONIC-THERAPEUTIC DELIVERY SYSTEM

[75] Inventors: Patrick S. L. Wong, Hayward; Felix Theeuwes, Los Altos, both of Calif.

[73] Assignee: ALZA Corporation, Palo Alto, Calif.

[21] Appl. No.: 665,332

[22] Filed: Oct. 26, 1984

[51] Int. Cl.$^4$ .......................... A61K 9/22; A61K 9/24
[52] U.S. Cl. .................................... 604/892; 428/508
[58] Field of Search ............... 604/896, 892; 428/510, 428/507, 508

[56] References Cited

U.S. PATENT DOCUMENTS 4,008,719 2/1977 Theeuwes et al. ................. 604/896
4,331,728 5/1982 Theeuwes ............................ 428/508

Primary Examiner—Howard S. Williams
Attorney, Agent, or Firm—Paul L. Sabatine; Edward L. Mandell; Steven F. Stone

[57] ABSTRACT

An osmotic device is disclosed for delivering a drug to the colon. The device comprises a laminated wall surrounding a compartment containing a drug with a passageway through the wall for dispensing the drug from the device. The laminated wall comprises three laminae, an inner semipermeable lamina, a middle lamina containing a salt of a fatty acid and an outer enteric lamina.

5 Claims, 5 Drawing Figures

U.S. Patent    Dec. 9, 1986    4,627,851
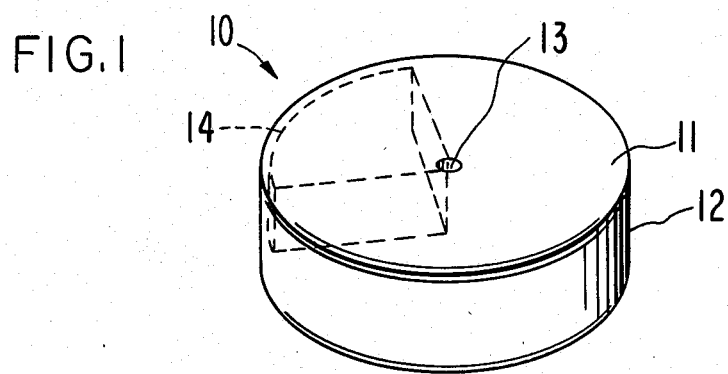
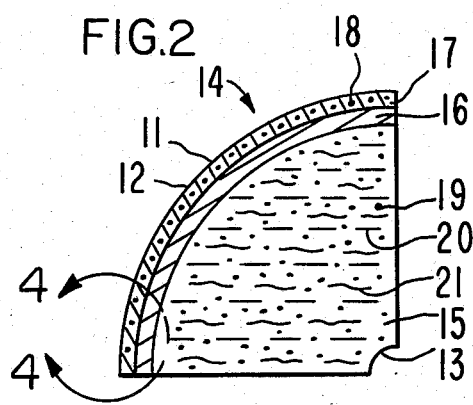 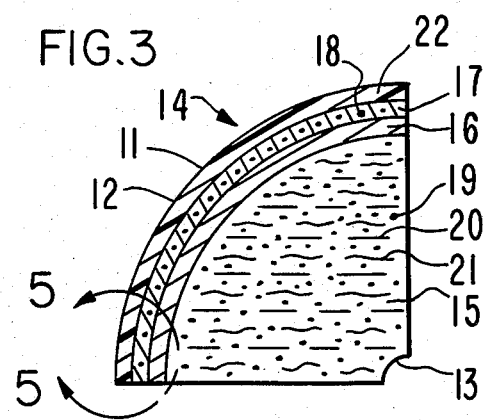
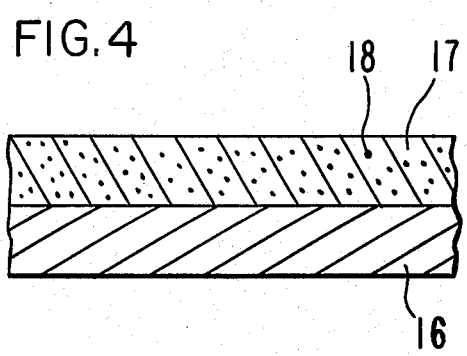 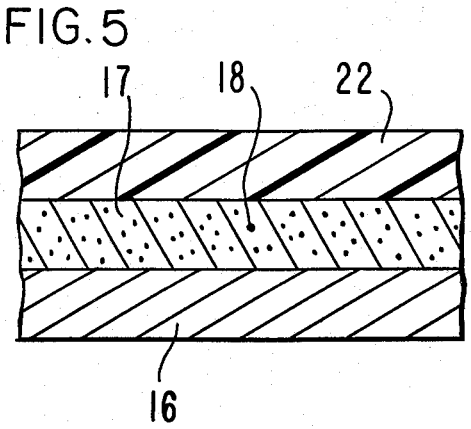

COLONIC-THERAPEUTIC DELIVERY SYSTEM

The present invention pertains to the administration of a beneficially active agent to a preselected region of the gastrointestinal tract, specifically the colon. More particularly, the invention relates to both a novel and useful osmotic delivery system and method for delivering by the oral route a beneficial agent to the colon. The invention concerns also laminates useful for manufacturing the osmotic delivery system.

BACKGROUND OF THE INVENTION

A critical and a continuous need exists for a delivery system for orally administering a beneficial agent in the colon. The oral delivery system is needed and it would be of a particular value in the management of ailments, diseases, or inflammation of the colon that require colon-targeted administration of a beneficially active agent. That is, the oral delivery system would have a therapeutic value where therapy indicates topical-colon administration of a beneficial agent to an affected colon site. A critical and a continuous need exists also for an oral delivery system that releases an active agent for systematic absorption of the active agent from the colon. The need for such a delivery system exists where it is therapeutically indicated to delay systemic absorption of the active agent for a predetermined period of time. More specifically, the need exists for a system that releases the active agent at about the time therapy is needed by a patient. An oral delivery system that releases an active agent for systemic absorption only in the colon at a preselected time would have a practical value in the management of patients with asthma, arthritis or inflammation. For example, the delivery system would be administered orally to the patient at bedtime with the system passing through the stomach and the intestine during the night and arriving at the colon, where it commences release in the colon the active agent in the morning, thereby providing the patient with the desired therapy at the appropriate time.

Prior to this invention, tablets, capsules, and the like, were orally administered for dispensing an active agent throughout the entire gastrointestinal tract. However, for some drugs a considerable amount of the active agent dispensed by the tablets and the capsules is inactivated by the stomach because of the acidic and enzymatic environment of the stomach. Additionally, most agents are metabolized or absorbed in the small intestine from such immediate release forms. Consequently, very little of the active agent is available for producing a therapeutic result in the colon. The delivery of active agents through the rectum using suppositories or enemas often leads to colon therapy; but rectal administration is inconvenient and messy, and it is not readily accepted by the patient population. Also, agent delivery from suppositories cannot reach most of the colon as it is self-limited to the immediate area of administration.

It is immediately self-evident in view of the above presentation, that a need exists for an oral system that delays the onset of delivery for a period of time for the system to reach the colon. Such a period of time corresponds to the time required for the system to transit through the stomach and small intestine and commence delivery of the active agent about the time the system arrives at the colon.

OBJECTS OF THE INVENTION

It is an immediate object of this invention to provide a novel osmotic dispensing system for dispensing a useful agent to produce a beneficial effect, which dispensing system overcomes the aforesaid disadvantages associated with the prior art dispensing systems.

It is another object of this invention to provide an osmotic delivery system, for the controlled delivery of a beneficial agent to the colon, and which delivery system represents an advancement in colon-specific therapy.

It is another object of this invention to provide an oral, osmotic delivery system manufactured in the form of an osmotic device for dispensing a beneficial agent to the colon of the gastrointestinal tract of an animal for both topical and systematic therapy.

It is another object of this invention to provide an osmotic delivery system that delays the onset of agent release from the system for a period of time that approximately corresponds to the time required for the osmotic system to passes through the stomach and the small intestine.

It is another object of this invention to provide a delayed-release osmotic system useful for topical-colonic therapy by the oral route.

It is another object of this invention to provide a delayed release osmotic system useful for releasing a drug in the colon for systematic absorption therefrom.

It is another object of this invention to provide an oral osmotic device comprising a compartment surrounded by a first wall formed of a semipermeable composition, and by a second wall formed of a fluid impermeable composition containing an osmotic solute with the device having an osmotic passageway through both walls.

It is another object of this invention to provide an osmotic device comprising a compartment surrounded by an inner wall formed of a semipermeable composition, a middle wall formed of a fluid impermeable composition containing an osmotic solute, an outer wall formed of an enteric composition, and a passageway through the walls for delivering a drug form the osmotic device.

It is another object of the invention to provide laminates useful for making osmotic delivery systems.

Other objects, features, aspects and advantages of this invention will be more apparent to those versed in the art from the following detailed specification taken in conjunction with the drawing figures and the accompanying claims.

BRIEF DESCRIPTION OF THE DRAWINGS

In the drawings, which are not drawn to scale, but are set forth to illustrate various embodiments of the invention, the drawing figures are as follows:

FIG. 1, is a view of an osmotic dispensing system designed for orally administering a beneficial agent such as a drug to the colonic region of the gastrointestinal tract. In FIG. 1 a portion of the delivery system is depicted in dashed lines for removing said portion to exhibit the structure of the delivery system;

FIG. 2 is a view of the portion depicted in FIG. 1, which portion is removed from the delivery system for illustrating an embodiment of the invention comprising a laminated wall, which system is useful for delivering a beneficial agent in the colon;

FIG. 3 is a view of the portion depicted in FIG. 1, removed from the delivery system for illustrating another embodiment of the invention comprising a three-layered laminated wall, and which system is useful for delivering a beneficial agent such as a drug to the colon;

FIG. 4 illustrates a laminate defining the structural member of the osmotic system taken through 4—4 of FIG. 2; and, FIG. 5 illustrates a laminate defining the structural member of the osmotic device taken through 5—5 of FIG. 3.

In the drawing figures and in the specification, like parts in related figures are identified by like parts. The terms appearing earlier in the specification and in the description of the drawing figures, as well as embodiments thereof, are further detailed elsewhere in the disclosure.

DETAILED DESCRIPTION OF THE DRAWINGS

Turning now to the drawings in detail, which drawings are examples of delivery systems provided by the invention and manufactured as osmotic delivery devices, and which examples are not to be construed as limiting, one example of an osmotic device is seen in FIG. 1, identified by the numeral 10. In FIG. 1, osmotic device 10 is sized, shaped and adapted for use as an orally administrable osmotic device, and it comprises a body member 11, a wall 12 and a passageway 13 in wall 12. FIG. 1 depicts also a section 14 that is a portion that can be cut from device 10 for illustrating the structural components of osmotic device 10.

In FIG. 2, a section 14 cut from the osmotic device of FIG. 1, is seen for illustrating the structural members of osmotic colonic delivery system 10. In FIG. 2, system 10 comprises body 11, wall 12, osmotic passageway 13, that extends through wall 12, and it connects an internal compartment 15 with the exterior of delivery system 10. Wall 12 of the osmotic system illustrated in FIG. 2, comprises a laminate formed of two lamina, an inner lamina 16 and an outer lamina 17. Inner lamina 16 is directly adjacent to compartment 15, and outer lamina 17 is adjacent to the exterior of osmotic system 10, positioned distant from compartment 15. Lamina 16, as seen in FIG. 2, comprises a semipermeable composition that is permeable to the passage of an external fluid present in the environment of use, such as aqueous and aqueous-like-fluids, such as biological fluids. Semipermeable lamina 16 is essentially impermeable to the passage of an active agent such as a drug. Lamina 16 is substantially inert, it maintains its physical and its chemical integrity during the dispensing of a beneficial drug, and it is non-toxic to animals, including humans. Lamina 16 is in laminar arrangement with laimina 17. Laimina 17 is made of a polymeric composition that is non-toxic, and preferably it is substantially impermeable to the passage of a beneficial agent such as a drug, and it is moderately permeable to the passage of fluids present in the environment of use. Lamina 17 is made from a different polymeric composition than the composition forming lamina 16. Lamina 17 additionally comprises a composition of matter 18 that is slightly soluble in the external fluid and it is slowly soluble, or slowly leached from lamina 17, when lamina 17 is contacted by an external fluid. Composition 18 can be homogeneously or heterogeneously dispersed throughout lamina 17. Usually, lamina 17 will contain from about 1 to 70 percent by weight of composition 18, and in a presently preferred embodiment, about 35 to 60 percent by weight.

Compartment 15, in one embodiment, contains a beneficial agent 19, represented by dots, that is soluble to very soluble in an external fluid imbibed into compartment 15, and it exhibits an osmotic pressure gradient across laminated wall 12 against an external fluid 20, indicated by dashes, that is imbibed into compartment 15. In another embodiment, compartment 15 contains a beneficial agent 19 that has limited solubility in fluid 20 imbibed into compartment 15, and in this instance it exhibits a limited osmotic pressure gradient across wall 12, mainly semipermeable lamina 16 against the external fluid 20. In this later embodiment, beneficial agent 19 optionally is mixed with an osmagent 21, indicated by wavy lines, that is soluble in the external fluid and it exhibits an osmotic pressure gradient across wall 12 against an external fluid.

FIG. 3 depicts another portion of yet another osmotic colon delivery system 10 provided by the invention. In FIG. 3, a portion 14 of osmotic system 10 is seen sectioned from a delivery system made in the manner of FIG. 1. In FIG. 3, portion 14 comprises body 11, wall 12, osmotic passageway 13, and internal compartment 15. Wall 12 of the osmotic system illustrated in FIG. 3 comprises a laminate formed initially of three laminae, an inner lamina 16, a middle lamina 17, and an outer lamina 22. Inner lamina 16 is adjacent to compartment 15 and outer lamina 22 faces the exterior of the system. Lamina 16 is formed of a semipermeable composition that is permeable to the passage of an external fluid and it is essentially impermeable to the passage of the active agent. Lamina 17 is in contacting laminar arrangement with lamina 16. Lamina 17 is formed of a polymeric composition substantially impermeable to the passage of a beneficial agent, and it has distributed therethrough a composition of matter 18 slightly soluble in external fluid. Lamina 22 is formed of an enteric material that does not dissolve or disintegrate in the stomach during the time the osmotic system remains in the stomach, and the enteric lamina disintegrates once osmotic system 10 enters the small intestine. Compartment 15 of osmotic device 10 comprises a beneficial agent 19, and, optionally, an osmotically effective compound. During operation, when the osmotic system 10 is in the environment of use dispensing beneficial agent 19, osmotic compartment 15 contains also imbibed external fluid 20. Generally, wall 12 comprises a semipermeable lamina of 25 to 500 microns, an osmotic lamina of 25 to 350 microns, and an enteric lamina of 25 to 200 microns.

FIG. 4 illustrates a view taken through 4—4 of FIG. 2. FIG. 4 depicts wall 12 comprising semipermeable lamina 16 in laminar arrangement with lamina 17 having homogeneously or heterogeneously dispersed throughout lamina 17 slightly aqueous soluble composition 18. FIG. 5 illustrates a view taken through 5—5 of FIG. 3. FIG. 5 depicts wall 12 comprising three-layers in contacting, laminar arrangement. As illustrated, wall 12 comprises semipermeable lamina 16, fluid path forming lamina 17 with composite 18 and enteric lamina 22.

Osmotic delivery system 10 as seen in FIGS. 1 through 3 can be made into many embodiments for oral use for releasing locally or systemically acting therapeutic medicaments in the colon of the gastrointestinal tract. The oral system can have various conventional shapes and sizes such as round with a diameter of $\frac{3}{16}$ inch to 9/16 inch, or it can be shaped like a capsule having a range of sizes from triple zero to zero and from 1 to 8.

In these manufactures, system 10 can be adapted for administering a beneficial agent to warm-blooded mammals, such as humans.

DETAILED DESCRIPTION OF THE INVENTION

In accordance with the practice of this invention, semipermeable lamina 16 is formed of a material that does not adversely affect the beneficial agent, and the animal host. The semipermeable laminaforming material is a polymer composition that is permeable to the passage of an external fluid such as water and aqueous biological fluids, while remaining substantially impermeable to beneficial agents and osmotic solutes. The selectively permeable materials forming semipermeable lamina 16 are materials that are insoluble in body fluids and they are non-erodible. Typical selective materials for forming lamina 16 include semipermeable polymers, also known to the art as osmosis membranes. The semipermeable polymers include cellulose acylate, cellulose diacylate, cellulose triacylate, cellulose ester, cellulose ether, and cellulose ester ester ether. Representative semipermeable polymers include cellulose acetate, cellulose diacetate, cellulose triacetate, dimethylcellulose acetate, cellulose acetate propionate, cellulose acetate butyrate, and the like. Semipermeable polymers are known in U.S. Pat. Nos. 3,173,876; 3,276,586; 3,541,005; 3,541,006; 3,546,142; 3,845,770; 3,916,899; 4,036,228; and 4,111 202.

Lamina 17, containing composition 18 is formed of a polymer that is substantially non-toxic, substantially non-erodible, impermeable to the passage of drug formulation and it is moderately permeable to the passage of fluid present in the environment of use. In operation, when lamina 17 is in the fluid environment of use, external fluid contacts the outer surface of lamina 17 amd slowly dissolves or slowly leaches composition 18 from lamina 17. The process is repeated during the period of time lamina 17 is exposed to external fluid. As the fluid removes composition 18 from lamina 17, the inward progressive removal of composition 18 causes fluid paths to be formed in lamina 17. The fluid paths provide a plurality of paths for external fluid to flow through to semipermeable lamina 16. This proceedure provides a source of fluid for the operation of semipermeable lamina 16, Exemplary materials for fabricating lamina 17 include a member selected from the group consisting of poly(olefins), poly(vinyls), poly(ethylenes), poly(propylenes), poly(styrenes), poly(acrylonitriles), poly(vinylidene halides) and copolymers thereof. Typical materials for fabricating lamina 17 include a member selected from the group consisting of ethylene-vinyl ester copolymers having an ester content of 4% to 80% such as ethylene-vinyl acetate copolymer, ethylene-vinyl hexanoate copolymer, ethylene-vinyl propionate copolymer, ethylene-vinyl butyrate copolmer, ethylene-vinyl pentantoate copolymer, ethylene-vinyl trimethyl acetate copolmer, ethylene-vinly diethyl acetate copolymer, ethylene-vinyl-3-methylbutanoate copolymer, ethylene-vinyl-3-dimethyl butanoate copolymer, and ethylene-vinyl benzoate copolymer. Additional exemplary materials suitable for manufacturing lamina 17 include acrylonitrile-methyl vinyl ether, vinyl chloride-diethyl fumarate, plasticized poly(vinyl chloride), plasticized poly(amides), poly(isoprene), poly(isobutylene), lightly cross-linked poly(vinyl pyrrolidone), vinyldiethyl fumarate copolymer, ethylene-propylene copolymer, and the like. The polymeric materials are known in U.S. Pat No. 4,190,642, and in *Handbook of Common Polymers* by Scott et al., 1971, published by CRC Press, Cleveland.

Lamina 22 is made from an enteric materials that do not dissolve or disintegrate in the stomach during the period of time the osmotic system passes through the stomace. The enteric materials suitable for forming enteric lamina 22 include: (a) enteric materials that are digestable by enzymes in the small intestine; (b) enteric materials containing an ioniazable polyacid; (c) enteric materials that are a long-chain polymer with an ionizable carboxyl group, and the like.

Representative enteric materials include: (d) a member selected from the group of phthalates consisting essentially of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ehter phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxpropl methylcellulose hexahydrophthalate, polyvinyl acetate phthalate, and the like; (e) a member selected from the group consisting of keratin, keratin sandarac-tolu, salol, salol β- napthyl benzoate and acetotannin, salol with balsam of Peru, salol with tolu, salol with gum mastic, salol and stearic acid, and salol and shellac; (f) a member selected from the group consisting of formalized protein, formalized gelatin, and formalized cross-linked gelatin and exchange resins; (g) a member selected from the group consisting of myristic acid-hydrogenated castor oil-cholesterol, stearic acid-mutton tallow, stearic acid-balsam of tolu, and stearic acid-castor oil; (h) a member selected from the group consisting of shellac, ammoniated shellac, ammoniated shellac-salol, shellac-wool fat, shellac-acetyl alcohol, shellac-stearic acid-balsam of tolu, and shellac-n-butyl stearate; (i) a member selected from the group consisting of abietic acid, methyl abietate, benzoin, balsam of tolu, sandarac, mastic with tolu, and mastic with acetyl alcohol; (j) a member selected from the group consisting of cellulose acetate with shellac, starch acetate phthalate, polyvinyl acid phthalate, 2-ethoxy-5-(2-hydroxyethoxy-methyl)-cellulose phthalic acid, acid phthalates of carbohydrates, zein, alkyl resin-unsaturated fatty acids-shellac, colophony, mixtures of zein and carboxymethylcellulose; and the like. The enteric materials are discussed in *Remington's Pharmaceutical Sciences,* 1965, 13th Ed., pages 604 to 605, published by Mack Publishing Co., Eaton, Pa.

The composition of matter 18 housed and distributed throughout lamina 17 in a preferred embodiment is a salt of a fatty acid. The salt is selected from the group consisting of alkali salt, or an alkaline earth salt. The presently preferred fatty acid has from 4 to 26 carbons, including both saturated and unsaturated fatty acids. Representative saturated fatty acids include a member selected from the group consisting of butyric, isolvaleric, capioic, caprylic, capric, lauric, myristic, palmitic, stearic, arachidic, behemic, lignoceric and cerotic. Representative unsaturated fatty acids include a member having 10 to 26 carbons and selected from the group consisting of docylenic, dodecylenic, palmitoleic, oleic, ricinoleic, petroselinic, vaccenic, linoleic, linolenic, eleostearic, licanic, parinaric, tariric, gadoleic, archidonic, cetoleic, selacholeic, and the like. The alkalies suitable for the present purpose include lithium, sodium, potassium and the like; members of the first group of the periodic system commonly known as alkali metals. The alkaline earths include the elements of second group in the periodic system such as calcium and barium. Exemplary salts of fatty acids include potassium oleate, potassium stearate, sodium stearate, sodium caprylate, sodium caprate, sodium laurate, sodium myristate, sodium oleate, sodium palmitate, potassium caprylate, potassium laurate, potassium oleate, calcium recinoleate, calcium linoleate, calcium linolenate, and the like. Composition 18 in lamina 17 includes also anionic, nonionic and cationic surfactants. Representative anionics include carboxylic acids and salts, sulfonic acids and salts, sulfuric acid esters and salts, phosphat esters and salts. Examples of more specific anionic agents include sodium lauryl sulphate, triethanolamine salt of lauryl sulphate, sodium salt of sulfated castor oil, potassium salt of sulfated ricinoleic acid, sodium octyl sulfate, potassium lauryl sulfate, lithium luryl sulfate, sodium cetyl sulfate, and the like. Representative nonionic agents include ethoxylated alkylphenols, ethoxylated aliphatic alcohols, ethoxylated fatty acids, and fatty acid amides. Examples of more specific nonionic agents include sorbitan nonolaurate, sorbitan mono-oleate, mannide mono-oleate, 1:1 capric-diethanolamide, 1:2 lauric acid-diethanolamide condensate, and the like. Representative cationic agents include aliphatiic mono-, di-, and polyamines, amine oxides, substitute amines, alkylammonium salts, salts of heterocylic amines, arcylammonium salts, and the like. Examples of more specific cationic agents include lauryldimithylbenzlammonium chloride, laurylisoquinolinium bromide, cetylpryidinium chloride, laurylpyridinium bisulphate, laurylpicolinium p-toluenesulfonate, and the like.

The osmotically effective compound, which is an osmotically effective solute, present in compartment 15 include a member selected from the group consisting of water-soluble inorganic salts and water-soluble organic salts that are individually selected from the group consisting of magnesium sulfate, magnesium chloride, sodium chloride, lithium chloride, potassium sulfate, sodium carbonate, sodium sulfite, lethium sulfate, sodium sulfate, potassium acid phosphate, choline chloride, and the like. The osmotically effective solute can be used in compartment 15 for delivering drugs of limited aqueous solubility. The amount of osmotic solute in compartment 15 generally is from 0.5% to 25% by weight. The osmotically effective compounds are known to the are in U.S. Pat. Nos. 4,177,256 and 4,449,983.

The expression osmotic passageway as used herein comprises means and methods suitable for releasing a beneficial agent 19 from compartment 15. The osmotic passageway or orifice will pass through the laminated wall for communicating with compartment 15. The expression for passageway includes passageways formed by mechanical drilling or laser drilling through the laminated wall. Generally, for the purpose of the invention, the passageway will have a maximum cross-sectional area, A, defined by the equation $$(L/F) \times (Qv/t) \times (1/DS) \qquad (1)$$

wherein L is the length of the passageway (Qv/t) is the mass delivery rate of agent D released per unit time, D is the diffusion coefficient of the agent in the release solution, S is the solubility of the agent in the fluid and F has a value of approximately 2 to 1000, said osmotic passageway having a minimum area, $A_S$, defined by the equation $$[(Lv/t) \times 8 \times (\pi\eta/\Delta p)]^{\frac{1}{2}} \qquad (2)$$

wherein L is the length of the passageway, v/t is the volume of the agent released per unit of time, is 3.14, is the viscosity of the solution being released, and P is the hydrostatic pressure difference between the inside and the outside of the compartment and having a value up to 20 atmospheres. The dimensions for the osmotic passageway if disclosed in U.S. Pat. No. 3,916,899.

The term beneficial agent as used in this specification and the accompanying claims includes drugs that are pharmacolohically active, that produce, when released in the colon, a local or a systemic beneficial, therapeutic effect. The active drug that can be delivered includes inorganic and organic beneficially active compounds, such as materials that act on the nervous system, hypnotics, sedatives, physic energizers, tranquilizers, anti-convulsants, muscle relaxants, anti-ulcer, anti-asthmatics, CSN stimulants, anti-parkinson agents, analgesics, anti-inflammatory, anesthetics, anti-microbials, anti-pyretics, and the like. The beneficial drugs are known to the medical are in *Pharmaceutical Sciences*, by Remington, 14th Ed., 1970, published by Mack Publishing Co., Easton Pa.; in *American Drug Index*, 1976, published by J. B. Lippincott Co., Philadelphia, Pa.; in *The Drug, The Nurse, The Patient, Including Current Drug Handbook*, 1974–1976, by Falconer et al., published by Saunder Company, Philadelphia, Pa., and in *Medical Chemistry*, 3rd Ed., Vols. 1 and 2, by Burger, published by Wiley-Interscience. New York.

The osmotic devices of the invention are manufactured as follows: In one embodiment, the drug is mixed with drug formulation ingredients by ballmilling, calendering, stirring, and pressing into preselected shape having a shape that corresponds to the shape of the final osmotic device. The semipermeable material forming the first lamina can be applied by dipping, molding, or spraying the pressed mixture. One procedure for applying a wall-forming material is the air suspension procedure. The air suspension technique can be used for manufacturing a wall formed of a single layer, or formed of a multiplicity of layers. The air procedure is desribed in U.S. Pat. No. 2,799,241; in *J. Am. Pharm. Assoc.*, Vol 48, pages 451 to 459, 1959, and ibid, Vol 49, pages 82 to 84, 1960. Procedures for measuring the surface area diameter of solutes are reported in *Journal Amer. Chem. Soc.*, Vol. 60, 309 to 319, 1938; *The Surface Chemistry of Solids*, by Gregg, 2nd Ed., 1961, published by Reinhold Corp., New York; *Absorption, Surface Area and Porosity*, by Gregg et al., 1967, published by Academic Press, New York; *Physical Absorption of Gases*, by Yound et al., 1962, published by Butterworth & Co., London; and *Fine Particle Measurements*, by Valla, 1959, published by Macmillan, New York. The osmotic pressure of solutes can be measured in a commercially available osmometer that measures the vapor pressure differences between pure water and the solution containing a solute to be analyzed, and according to standard thermodynamic principles, the vapor pressure ratio is converted into osmotic pressure difference. An osmometer that can be used for osmotic pressure measurements is identified as Model 302B, Vapor Pressure Osmometer, manufactured by the Hewlett Packard Co., Avondale, Pa. Procedures for measuring aperture formation in lamina 16 by osmotic solute generating hydrostatic pressure in depot 17 exceeding the cohesive integrity of the polymer with the formation of fluid channels can be determined by measurements predicated on pressure deflection and mechanical behavior measurement techniques are reported *Modern Plastics*, Vol. 41,143 to 144, 146 and 182, 1964; *Handbook of Common Polymers*, by Scott et al., 588 to 609, 1971, published by CRC Press, Cleveland, Ohio; *Machine Design*, 107 to 11, 1975; *J. Sci. Instruments*, Vol. 42, 591 to 596, 1965; and by measuring mechanical stress-strain patterns of polymers using the Instron ® Testing Machine, available from instron Corp., Canton, Mass.; and by using the procedures disclosed in U.S. Pat. Nos. 4,177,256; 4,190,642; 4,298,003; and 4,265,874.

Exemplary solvents suitable for manufacturing the walls include inert inorganic and organic solvents that do not adversely harm the wall forming materials, the drug, the agent, and the final device. The solvents broadly include aqueous slovents, alcohols, ketones, esters, ethers, aliphatic hydrocarbons, halogenated solvents, cycloalphatic aromatics, heterocyclic solvents, and mixtures thereof. Typical solvents include acetate, ethyl acetate, methyl isobutyl ketone, n-hexane, ethylene glycol monoethyl acetate, carbon tetrachloride, methylene chloride, ethylene dichloride, proplene dichloride, cyclohexane, mixtures such as acetone and water, acetone and methanol, acetone and ethyl alcohol, methylene dichloride and methanol, ethylene dichloride and methanol, and mixtures thereof.

The following example is merely illustrative of the present invention, and it should not be considered as limiting the scope of the invention in any way, as this example and other equivalents thereof will become more apparent to those versed in the art in the light of the present disclosure, the drawings and the accompanying claims.

An oral osmotic device for the delivery of 5-aminosalicylic acid to the colon is made as follows: A drug composition is prepared for housing in the compartment of an osmotic device by thoroughly blending 200 mg of 5-amino salicylic acid, 20 mag of lactose, 10 mg of polyvinyl pyrrolidone, 20 mg of sodium chloride and 3 mg of magnesium stearate, and then compressing the homogeneous blend into a precompartment-forming drug formulation. Next, the compressed drug formultion is placed in an air suspension machine and coated with a semipermeable lamina-forming composition. The semipermeable laminaforming composition comprises 80% by weight of cellulose acetate having an acetyl content of 39.8% and 20% by weight of cellulose acetate having an acetyl content of 32%. The semipermeable lamina is applied from a solvent mixture comprising methylene chloride and 95% ethanol, 80:20, wt:wt. The semipermeable lamina coated compartment is air dried in a force air oven at 50° C. over night.

Next, a slurry of ethylene-vinyl acetate copolymer having a vinyl acetate content of 40% is prepared by mixing the copolymer in methylene chloride and adding thereto 35 g of sodium lauryl sulfate. Then, the above-prepared semipermeable-limina coated compartment is submerged into the copolymer slurry and a layer of the copolymer containing the anionic sodium lauryl sulphate is coated onto the exterior surface of the semipermeable cellulose acetate. The laminated coated compartment is dried in a forced air oven at 50° C. for about 18 hours. Next, an enteric lamina is applied by placing the two-layered laminated-coated compartments into a pan containing shellac. The pan is prepared by pouring a quantity of shellac, U.S.P. grade, into a pan sufficient to thoroughly wet the entire surface of the ethylene-vinyl acetate copolymer lamina. After the entire surface is coated with the shellac, the shellac coated drug compartments are removed from the pan and dried at 50° C. Then, the dry drug compartments again are placed in the pan, and more shellac is added to the pan, and another coating is applied to form the lamina. The three-layered compartments are dried in a forced air oven at 50° C. for one week. Then an osmotic passageway is laser drilled through the three laminae connecting the compartment with the exterior of the device. The osmotic passageway has a diameter of 9 mils for delivering the drug from the device.

An oral osmotic device for the delivery of 5-aminosalicylic acid to the colon is prepared by following the above procedure with all conditions as previously described, except that sodium lauryl sulfate is replaced with 45 g sodium stearate.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

We claim:

1. An osmotic device for delivery a drug to a biological environment of use, said device comprising:
   (a) a shaped laminated wall comprising: (1) a first lamina comprising a semipermeable composition permeable to the passage of fluid and substantially impermeable to the passage of drug; (2) a second lamina comprising a polymer and a salt of a fatty acid, said second lamina permeable to the passage of fluid; and a third lamina comprising a member selected from the group consisting of cellulose acetyl phthalate, cellulose diacetyl phthalate, cellulose triacetyl phthalate, cellulose acetate phthalate, hydroxypropylmethyl cellulose phthalate, cellulose ester phthalate, cellulose ether phathalate, sodium cellulose acetate phthalate, methyl cellulose phthalate, and hydroxypropl cellulose phthalate; said laminated wall surrounding and defining:
   (b) a compartment containing a dosage amount of a beneficial drug formulation; and,
   (c) at least one passageway through the laminated wall communicating with the compartment and the exterior of the osmotic device for dispensing the drug formulation from the device to the environment of use.

2. An osmotic device for delivering a drug to a biological environment of use, said device comprising:
   (a) shaped laminated wall comprising: (1) a first lamina comprising a semipermeable composition permeable to the passage of fluid and substantially impermeable to the passage of drug; (2) a second lamina comprising a polymer and a surfactant selected from the group consisting of nonionic, anionic and cationic surfactants, said second lamina permeable to the passage of fluid; and a third lamina comprising a member selected from the group consisting essentially of cellulose acetyl phthalate, cellulose diacetyl phthalste, cellulose triacetyl phthalate, cellulose acetate phthalate, hydroxyproplmethyl cellulose phthalate, cellulose ester phthalate, cellulose ether phthalate, sodium cellulose acetate phthalate, methyl cellulose phthalate and hydroxpropyl cellulose phthalate;

(b) a compartment containing a dosage amount of a beneficial drug formulation; and, (c) at least one passageway through the laminated wall communicating with the compartment and the exterior of the osmotic device for dispensing the drug formulation from the device to the environment of use.

3. A three-layered laminate useful for forming an osmotic drug delivery device, wherein the laminate comprises a first layer comprising a member selected from the group consisting of cellulose acylate, cellulose diacylate, cellulose triacylate, cellulose ester, cellulose ether, and cellulose ester ether; a second layer comprising a member selected form the group consisting of a poly(olefin), poly(vinyl), ethylene vinyl acetate copolymer, poly(styrene), poly(acrylonitrile), ethyl cellulose, poly(vinylidene halide) and a salt of a fatty acid; and a third layer comprising a member selected from the group consisting of cellulose acetyl phthalate, cellulose diacetyl phthalate, cellulose triacetyl phthalate, cellulose ester phthalate, cellulose ether phthalate, and cellulose ester ether phthalate.

4. A three-layered laminae useful for forming an osmotic drug delivery device, wherein the laminae comprises a first layer comprising a membr selected from the group consisting of cellulose acylate, cellulose diacylate, cellulose triacylate, cellulose ester, cellulose ether, and cellulose ester ether; a second layer comprising a member selected from the group consisting of poly(olefin), poly(vinyl), ethylene vinyl actate copolymer, poly(styrene), poly(acrylonitrile), ethyl cellulose, poly(vinylidne halide) and a member selected from the group consisting of a nonionic, cationic and anionic surfactant; and a third layer comprising a member selected from the group consisting of cellulose acetyl phthalate, cellulose diacetyl phthalate, cellulose triacetyl phthalate, cellulose ester phthalate, cellulose ether phthalate, and cellulose ester ether phthalate.

5. A two-layered laminae useful for forming a drug delivery device, wherein the laminae comprise a lamina comprising a member selected from the group consisting of a poly(olefin), poly(vinyl), ethylene vinyl acetate copolymer, poly(styrene), poly(acrylonitrile), poly(vinylidene halide) snd a vinyl ester copolymer, said lamina in laminar arrangement with a lamina comprising a member selected from the group consisting of a cellulose acetyl phthalate, cellulose diacetyl phthalate, cellulose triacetyl phthalate, cellulose ester phthalate, cellulose ether phthalate, and polyvinyl acetate phthalate.

* * * * *